US006033389A

United States Patent [19]
Cornish

[11] Patent Number: 6,033,389
[45] Date of Patent: *Mar. 7, 2000

[54] EYE MEDICAMENT DISPENSING DEVICE

[76] Inventor: Brian K. Cornish, P.O. Box 2010, Palm Harbor, Fla. 34682

[*] Notice: This patent is subject to a terminal disclaimer.

[21] Appl. No.: 08/752,824

[22] Filed: Nov. 20, 1996

Related U.S. Application Data

[63] Continuation of application No. 08/539,794, Oct. 1, 1995, Pat. No. 5,578,021.

[51] Int. Cl.⁷ .................................................. A61M 35/00
[52] U.S. Cl. ............................................ 604/300; 604/301
[58] Field of Search .................................... 604/294–296, 604/300–302; 222/420–422

[56] References Cited

U.S. PATENT DOCUMENTS

| | | | |
|---|---|---|---|
| 2,320,070 | 5/1943 | Derham et al. | 604/295 |
| 2,919,696 | 1/1960 | Rinaldy | 604/301 |
| 3,945,381 | 3/1976 | Silver | 604/301 |
| 4,338,936 | 7/1982 | Nelson | 604/300 |
| 4,629,456 | 12/1986 | Edwards | 604/300 |
| 5,053,188 | 10/1991 | Goddard | 604/300 |
| 5,382,243 | 1/1995 | Mulholland | 604/301 |
| 5,611,788 | 3/1997 | Marchment | 604/300 |

*Primary Examiner*—John G. Weiss
*Assistant Examiner*—David J. Cho
*Attorney, Agent, or Firm*—Eugene E. Renz, Jr.

[57] ABSTRACT

An eye medicament dispensing device utilizing a container having a chamber for storing air. The container possesses an outlet for passing the air from the container. A cup structure, connected to the container, is fitted over the eye and has an open cavity formed by a base, a wall portion extending from the base, and a terminal continuous edge portion. The terminal continuous edge portion is intended for contacting and holding open the upper and lower eyelids. The eye cup structure also is formed with an outer surface, an inner surface, and an opening or bore therebetween. The opening is positioned at the base of the eye cup and is surrounded by indicia on the inner surface of the eye cup at a selected distance from the base opening. The indicia essentially surrounds the base and may take the form of a continuous design or an interrupted design. Medicament is guided from the container through the opening in the base of the eye cup toward the eye held in the eye cup by the use of an orifice.

4 Claims, 1 Drawing Sheet

EYE MEDICAMENT DISPENSING DEVICE

This is a continuation of copending application(s) Ser. No. 08/539,794 filed Oct. 1, 1995 now U.S. Pat. No. 5,578,021.

BACKGROUND OF THE INVENTION

The present invention relates to a novel and useful eye medicament dispensing device.

Many systems and apparatuses have been devised to apply solutions to the eye for the purpose of medical treatment, washing, and the like. For example, U.S. Pat. Des. Nos. 102,769 and 1,900,201 show eye cups for this purpose. The latter patent describes an eye cup having a bulb which mixes a stream of air through liquid for the purposes of agitation.

U.S. Pat. No. 5,201,726 shows an eye bath device which delivers a spray in a generally horizontal stream and includes a cup which surrounds the eye to confine the stream to the vicinity of the eye.

U.S. Pat. No. 4,605,398 describes an eye dropper having an averting member to keep the lower eye lid from blocking the eye while the drops are directed into the eye.

Design Pat. Des. No. 330,418 and U.S. Pat. Nos. 4,543,096; 4,733,802; 4,960,407; 5,037,406; 5,178,613; and 5,382,243 describe eye droppers which utilize an eye cup as well as a dispenser that is generally in the form of a squeezable bottle.

U.S. Pat. Nos. 5,030,214 and 5,366,448 show eye drop delivery systems which include guides and dispensers which tend to direct the solution in the form of a spray rather than eye drops, such spray generally includes a horizontal component of travel.

U.S. Pat. Nos. 5,154,710 and 5,154,711 show ophthalmic delivery devices that include an eye cup having an aperture through the cup which allows the user to look at a target external to the eye cup while the eye drop is dispensed.

U.S. Pat. No. 4,338,936 shows a device and method for delivering finely divided solid medication to the eye utilizing a squeeze bottle. The solid material is directed horizontally at the eye and quickly dissolves in the tear fluid to produce the proper dosage necessary for an eye treatment.

An eye medicament dispensing device which is capable of delivering finely divided solids to the eye safely and accurately would be a notable advance in the medical field.

SUMMARY OF THE INVENTION

In accordance with the present invention a novel and useful eye medicament dispensing device is herein provided.

The device of the present invention utilizes a container having a chamber for storing the solid medicament in finely divided form, similar to the medicament shown in U.S. Pat. No. 4,338,936, incorporated by reference in whole, in this application. The container includes an outlet for passing the solid medicament from the container to the eye in a particular dosage. The solid medicament would be delivered in a single dose through a single squeeze of the container, which may be a flexible body.

The container is also provided with a cup structure which fits over the eye and is connected to the container. The cup structure has an open cavity formed by a base, a wall portion extending from the base, and a terminal, continuous edge portion. The continuous edge portion is intended for contacting the upper and lower eye lids and holding such lids open while the medicament passes from the container to the eye.

Cup structure also includes an outer surface and an inner with an opening or bore between the two surfaces. The opening terminates on the inner surface at the base of the eye cup. The inner surface is provided with indicia in surrounding relationship to the opening through the base of the eye cup and at a selected distance from the opening in the base of the eye cup. The surrounding indicia may be a continuous line, a series of marks, or combination of the two.

Storing means, which may be in the form of a filter in the air passageway from the container, holds a particular dosage of medicament.

Conducting means is also found in the present invention for guiding the medicament from the storing means through the opening in the base of the eye cup into the eye. Such conducting means may include a member which provides a passageway from the container and projects into the open cavity from the base of the cup structure. The member includes an orifice which communicates with the chamber and the cup structure. The storing means may be located with the passageway of the member.

It may be apparent that a novel and useful eye medicament dispensing device is herein provided.

It is therefore an object of the present invention to provide an eye medicament dispensing device which is capable of delivering finely divided solid material to the eye accurately and safely.

Another object of the present invention is to provide an eye medicament dispensing device which increases the safety of manipulating a conventional eye medicament dispenser.

A further object of the present invention is to provide an eye medicament dispensing device which includes a cup structure that effectively maintains the upper and lower eye lids in a position to allow medicament to be delivered through a nozzle to the corneal surface of the eye.

A further object of the present invention is to provide a medicament dispensing device for use with an eye that may be easily used and is disposable following use.

The invention possesses other objects and advantages especially as concerns particular characteristics and features thereof which should be apparent as the specification continues.

For a better understanding of the invention reference is made to the following detailed description of the preferred embodiments thereof which should be taken in conjunction with the hereinabove describe drawings.

DETAILED DESCRIPTION OF THE PREFERRED EMBODIMENTS

Various aspects of the present invention will evolve from the following detailed description of the preferred embodiments thereof which should be referenced to the prior described drawings.

Figure 1:
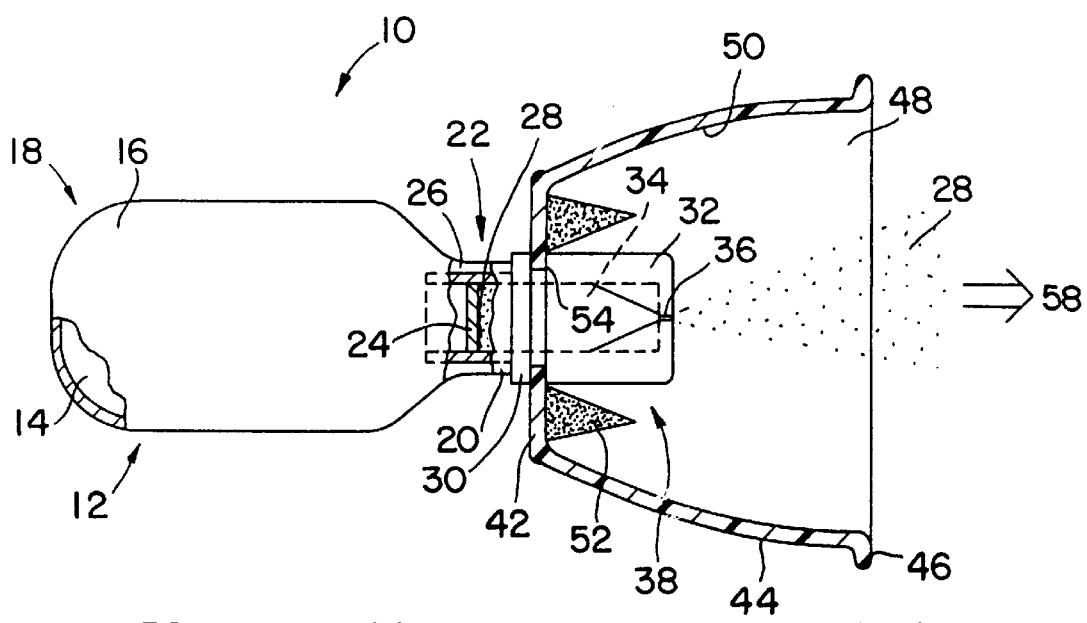
FIG. 1 is a side elevational view of the device with the eye cup depicted in section.

The invention as a whole is shown in the drawings by reference character 10. The eye medicament dispensing device 10, FIG. 1, includes as one of its elements a container 12 having a chamber 14 (broken away portion of FIG. 1) within a wall portion 16. Container 12 may be constructed of elastomeric material such as rubber, plastic, a composite, and the like. In any case, container 12 is meant to be squeezed by a user to evacuate air and a medicament which may be stored therein or in the evacuation path of exiting air which will be more fully discussed hereinafter. Container 16 is also formed into a body portion 18 terminating in a mouth 20 which includes an outlet for the air within container chamber 14.

Although storing means for the medicament 28 could lie within container 12, storing means 22 is shown in the preferred embodiments as taking the form of a filter 24. Filter 24 is wedged in a tube member 26 which fits within mouth 20 of container 12. Filter 24 includes a layer of medicament 28 which is in the form of finely divided solid material. Reference is again made to U.S. Pat. No. 4,338,936 with respect to the finely divided solid medicament and a system similar to filter 24. Tube 26 further possesses an intermediate flange 30 and an enlarged end portion 32. Passageway 34 of tube member 26 communicates with chamber 14 of container 12 and terminates in an orifice 36. Thus, tube member 26 serves as conducting means 38 for guiding air from container 12 and medicament from storing means 22 to and through orifice 36.

Eye cup structure 40 is linked or connected to the container 12 by intermediate tube member 26. That is to say, eye cup structure includes a base portion 42 and a wall portion 44 extending from base portion 42. Wall portion 44 extends from base portion 42 to a terminal edge portion 46 which is continuous. Wall portion 44 forms an open cavity 48. Wall portion 44 also includes inner surface 50 having an indicia 52 applied thereupon, FIG. 1. It should be noted that base 42 includes an opening 54 for accommodating tube member 26. The resultant structure permits enlarged end portion 32 of tube member 26 to extend into cavity 48 of eye cup structure 40, such that orifice 36 lies a specific distance from eye 62.

Figure 2:
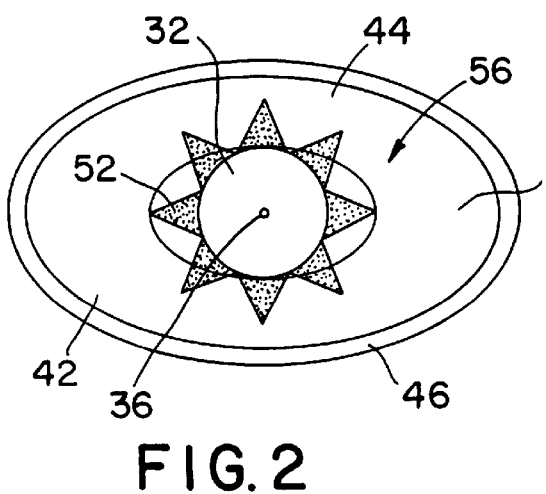
FIG. 2 is a front elevational view of the device of the present invention.

Indicia 52 is specifically located a selected distance from cup structure opening 54 in an essentially surrounding relationship therewith. As depicted in FIG. 2, indicia 52 takes the form of a series of triangle-like members 56 having apexes pointing toward edge portion 46 of cup structure 40. Other indicia suitable for the purpose of the present invention in surrounding relationship with opening 54 include a series of dots, a zig-zag, a continuous line in the form of an oval, and the like. Wall portion 44 may be formed of transparent or translucent material to emphasize indicia 52, in this case. Indicia 52 is intended to be seen by the eye when cup structure 40 fits over the eye in order to center orifice 36 on eye 62 during use in order to deliver medicament 28 to eye 62, directional arrow 58, FIG. 1.

Figure 2A:
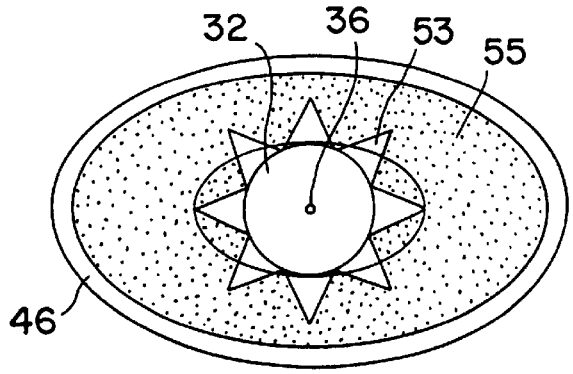
FIG. 2A is a front elevational view of the device of the present invention with an alternate indicia structure.

FIG. 2A draws an alternate indicia 53 which is formed of light coloration or by rendering wall 44 transparent. Inner surface 55 of wall 44 may be colored or rendered opaque to further contrast indicia 53.

Figure 3:
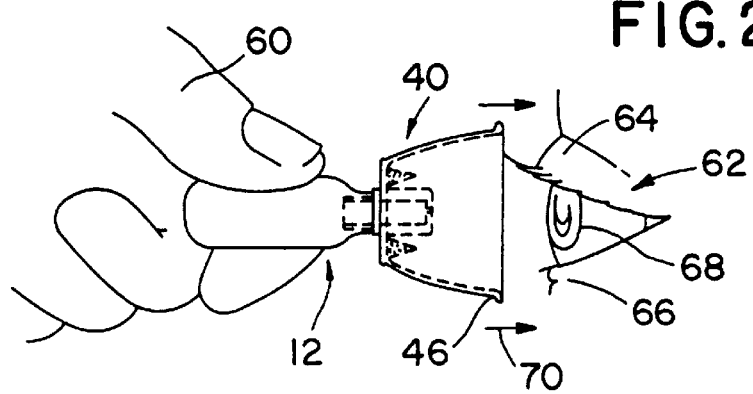
FIG. 3 is a side elevational view of the device of the present invention in use on a human eye.

In operation, turning to FIG. 3, the user's hand 60 grasps container 12 and directs eye cup structure 40 to a position over eye 62. Edge portion 46 of cup structure 40 is intended to engage the upper lid 64 and the lower lid 66 of eye 62, to maintain the eye 62 in an open position. Thus, cornea 68 is exposed to receive medicament 28 from device 10. Directional arrows 70 indicate the movement of device 10 toward eye anatomy 62. When edge portion 46 of eye cup structure 40 is in place on upper and lower lids 64 and 66 of eye anatomy 62. Orifice 36 lies a predetermined distance from cornea 68. The user then squeezes container 12. Squeezing container 12 evacuates air from chamber 14 of container 12, through filter 24, and through the orifice 36 of tube member 26. In addition, medicament 28 lying on filter 24 passes through orifice 36 and enters chamber 48 of eye cup structure 40. Directional arrow 58 indicates that medicament 28 then passes to the cornea 68 of eye anatomy 62. After delivery of medicament 28 to cornea 68 of eye anatomy 62, device 10 is then discarded. It has been found that indicia 52 allows the patient to accurately center orifice 36 on the central portion of cornea 68 of eye 62. In this manner, medicament is accurately delivered. Eye cup structure 40 also prevents end portion 32 of tube member 26 from touching cornea 68 and serves to maintain the aforementioned predetermined distance between orifice 36 and cornea 68 to produce a proper spray pattern of medicament 28 on cornea 68. Moreover, eye cup structure 40 also confines medicament 28 to cavity 48 during use.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

I claim:

1. A cup for use with a container for an eye medicament having a discharge orifice comprising:

A) a base having an opening for the container;

B) a wall portion extending from said base having a continuous terminal edge for contacting the upper and lower eye lids; and C) positioning means for centering the discharge orifice of the container on the eye comprising triangularly-shaped indicia on the inner surface of said cup, said indicia having apexes pointing toward the edge of the cup and having a portion lying a selected distance from said orifice, said indicia portion being positioned in an essentially surrounding relationship to said opening in said base, said inner surface of said cup and indicia being of a contrasting finish to emphasize said indicia and attract the eye of a user.

2. A cup as claimed in claim 1 wherein the wall surrounding the indicia is transparent and said indicia is formed of light coloration.

3. A medicament dispensing device comprising:

A) a container having a chamber or air and including an outlet for passing the air from the container;

1) a cup for use with a container containing an eye medicament
2) a base having an opening for the container;
3) a wall portion extending from said base, and a terminal continuous edge portion, said terminal continuous edge portion intended for contacting the upper and lower eye lids, said cup structure further included an outer surface, an inner surface and an opening therebetween, said opening positioned at said base of said eye cup;
4) positioning means for centering the discharge orifice of the container on the eye comprising triangularly-shaped indicia on the inner surface of said cup, said indicia having apexes pointing toward the edge of the cup and having a portion lying a selected distance from said orifice, said indicia portion being positioned in an essentially surrounding relationship to said opening in said base, said inner surface of said cup and indicia being of a contrasting finish to emphasize said indicia and attract the eye of a user.

B) storing means for holding the medicament in the path of air exiting said container; and C) conducting means for guiding the air from said container outlet and the medicament through said opening in said base of said eye cup, said conducting means including an orifice for directing the medicament to the eye.

4. A medicament dispensing device as claimed in claim 3 wherein the wall surrounding the indicia is transparent and said indicia is formed of light coloration.

* * * * *